United States Patent

Patmore et al.

[11] 3,954,850
[45] May 4, 1976

[54] CARBOXYLATION OF COMPOUNDS

[75] Inventors: Edwin L. Patmore, Fishkill; William R. Siegart; Harry Chafetz, both of Poughkeepsie, all of N.Y.

[73] Assignee: Texaco Inc., New York, N.Y.

[22] Filed: Feb. 3, 1971

[21] Appl. No.: 119,431

Related U.S. Application Data

[62] Division of Ser. No. 784,901, Dec. 18, 1968, Pat. No. 3,595,907.

[52] U.S. Cl.................. 260/514 G; 260/533 N; 260/533 R
[51] Int. Cl.².......................................... C07C 51/15
[58] Field of Search .................................. 260/514

[56] References Cited
UNITED STATES PATENTS

| | | | |
|---|---|---|---|
| 2,781,397 | 2/1957 | Wiese et al. | 260/514 |
| 3,275,686 | 9/1966 | Kurtz | 260/533 |

FOREIGN PATENTS OR APPLICATIONS

| | | | |
|---|---|---|---|
| 197,943 | 6/1967 | U.S.S.R. | 260/468 |

OTHER PUBLICATIONS

Kracch et al., Organic Name Reactions, pp. 273–274 (1964).

*Primary Examiner*—Robert Gerstl
*Attorney, Agent, or Firm*—T. H. Whaley; C. G. Ries; Robert A. Kulason

[57] ABSTRACT

Method of carboxylating a compound of the group of $R-C \equiv CH$, $RCH_2CN$, indene, cyclopentadiene or fluorene, where R is hydrocarbyl, comprising contacting said compound with carbon dioxide under substantially anhydrous conditions in the presence of a base of the formula:

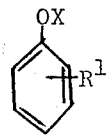

where X is sodium or potassium, $R^1$ is hydrogen or alkyl and subsequently acidifying the resultant reaction product to form the carboxylated product.

4 Claims, No Drawings

CARBOXYLATION OF COMPOUNDS

This is a division of Ser. No. 784,901, filed Dec. 18, 1968, now U.S. Pat. No. 3,595,907.

BACKGROUND OF INVENTION

The subject invention is found in the field of art relating to the introduction of a carboxylic acid group into organic compounds.

In the past, in order to carboxylate starting compounds contemplated herein by contacting with carbon dioxide, the contacting had to be accomplished in the presence of expensive bases such as sodium, naphthalene, n-butyl lithium and sodium hydride. Due to the cost of the base, the prior art methods of carboxylating starting reactants had only limited commercial prospects.

SUMMARY OF INVENTION

We have discovered a method of carboxylating organic compounds of the group of $RC \equiv CH$, $RCH_2CN$, indene, cyclopentadiene or fluorene, where R is alkyl, aryl, alkaryl and aralkyl of from 1 to 20 carbons consisting essentially of contacting said organic compounds with carbon dioxide under substantially anhydrous conditions in the presence of a base of the formula:

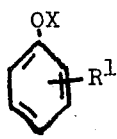

where X is sodium or potassium and $R^1$ is hydrogen or alkyl of from 1 to 12 carbons, and subsequently acidifying the resultant reaction mixture to recover the carboxylic acid. The discovery that the sodium and potassium phenoxide salts facilitate the production of carboxylated products in high yields has rendered a base catalyzed carboxylation process for the starting materials contemplated herein commercially feasible since the phenoxide is many times less expensive than the previous bases employed.

DETAILED DESCRIPTION OF THE INVENTION

Specifically, the invention relates to contacting essentially in the absence of water an active hydrogen containing organic compound of the group $R-C \equiv CH$, $RCH_2CN$, indene, cyclopentadiene or fluorene with a phenoxide of the formula:

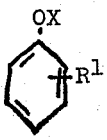

where R, $R^1$ and X are as heretofore defined with carbon dioxide preferably in excess and subsequently acidifying the resultant mixture to respectively form carboxyl compounds of the group of $R-C \equiv C-COOH$,

indene-3-carboxylic acid, tricyclo[$5.2.1.0^{2,6}$] deca-3,8-diene-4,9-dicarboxylic acid and tricyclo[$5.2.1.0^{2,6}$] deca-3,8-diene-5,5-dicarboxylic acid, or fluorene-9-carboxylic acid. The carbonation advantageously takes place at a temperature between about 0° and 150°C., preferably between about 25° and 50°C., under a carbon dioxide pressure of between about 1 to 200 atmospheres, preferably between 1 and 25 atmospheres, utilizing a mole ratio of phenoxide to organic compound of between about 1:1 and 20:1, preferably between 1:1 and 5:1, and an excess of carbon dioxide. Advantageously, the reaction mixture is acidified desirably at a temperature between about 5° and 35°C. to a pH of less than 6, preferably between about 1 and 3, to insure complete conversion of the intermediate alkali metal salt to the desired acid product. Although the reaction may be conducted in the absence of solvent, an inert liquid solvent is preferably used in amounts of between about 50 and 90 wt. % of the reaction mixture. The use of solvent is desirable in order for the production of maximum product yields.

By the term "substantially anhydrous" a water content of less than about 0.5 wt. % based on the reaction mixture during carbonation is intended.

Examples of the organic reactant compounds contemplated herein are phenylacetylene, benzyl cyanide, acetonitrile, hexanenitrile, acetylene, 1-butyne and 1-hexyne.

Examples of the base constituents are potassium and sodium salts of phenol, methylphenol, t-octylphenol, nonylphenol and dodecylphenol.

Specific examples of the acidifying acids contemplated herein are the mineral acids such as hydrochloric acid, nitric acid, sulfuric acid and hydrobromic acid in aqueous concentrations ranging from 4 to 96 wt. %.

Specific members of the inert liquid solvents contemplated herein are N,N-dimethylformamide, hexamethylphosphoramide, dimethyl sulfoxide, diphenyl sulfoxide, dimethyl sulfone and N,N-dimethylacetamide. The solvent during the carbon dioxide contact advantageously constitutes between about 50 and 90 wt. % of the reaction mixture.

During the carbon dioxide contact the gas is normally passed through the reaction mixture in a liquid state. However, alternatively, the organic reaction mixture may be sprayed into an atmosphere of carbon dioxide or the carbon dioxide may be passed over a solid or liquid surface which is desirably continually changed by agitation in order to form a fresh surface for contact.

The carboxylic acid products are recovered from the reaction mixture by standard means such as selective extraction, distillation, decantation and combinations thereof. Specific examples of the carboxylic acid products contemplated herein are indene-3-carboxylic acid, tricyclo [$5.2.1.0^{2,6}$] deca-3,8-diene-4,9-dicarboxylic acid and tricyclo [$5.2.1.0^{2,6}$] deca-3,8-diene-5,5-dicarboxylic acid, phenylpropiolic acid α-phenylcyanoacetic acid, cyanoacetic acid, α-cyanohexanoic acid, 9-fluorene carboxylic acid, 2-butynoic acid, 2-propynoic acid and 2-hexynoic acid.

The following examples further illustrate the invention but are not to be considered as limitations thereof.

EXAMPLE I

This example illustrates the preparation of indene-3-carboxylic acid from indene.

To a 3-necked round bottomed flask equipped with magnetic stirrer, thermometer, water cooled condenser and a gas sparger, the condenser connected to a mercury bubbler to protect the system from atmosphere, 3.5 grams of indene, 15.8 grams of potassium phenoxide, and 75 mls. of dimethylformamide were charged. The resultant mixture had a water content of less than 0.5 wt. %. An excess of dried carbon dioxide was bubbled through the reaction mixture under atmospheric pressure over a period of 5 hours. At the inception of carbon dioxide introduction, the reaction mixture was at room temperature (about 26°C.). The temperature increased from room temperature to 45°C. within 5 minutes after introduction. Within 8 minutes after introduction the temperature dropped to 28°C. and thereafter remained during the entire reaction period between 26° and 28°C.

At the end of the 5 hour period the reaction mixture was poured into a mixture of 80 mls. of concentrated hydrochloric acid and 100 grams of ice overlaid with 100 mls. of ether. The temperature of acidification was about 15°C. The layers were separated and the aqueous layer extracted with ether (5×100 mls.). The ether extracts were combined with the first organic layer. The combined ether organic layers were extracted, 10 wt. % sodium bicarbonate (5×100 mls) and the sodium bicarbonate extracts were then acidified (to a pH of 1 to 3) with 6M HCl while keeping the entire mixture cooled in an ice-water bath. The combined acidified sodium bicarbonate extracts were then extracted into ether (5×100mls), dried and the ether removed on a rotary evaporator to give the crude carboxylated product. Recrystallization of the crude product from benzene gave a yield of 1.79 grams of indene-3-carboxylic acid corresponding to a yield of 37.4 mole %. The structure of the indene-3-carboxylic acid product was confirmed by its melting point of 157°C. (lit. 158°–160°C.) and its infrared and nuclear magnetic resonance spectra.

EXAMPLE II

This is a description of the preparation of phenylpropiolic acid from phenylacetylene.

The carbon dioxide contact, acidification and recovery was the same as that used in Example I with the following exceptions:

To the 3-necked flask there was charged 3.1 grams of phenylacetylene, 15.8 grams potassium phenoxide and 75 mls. of dimethylformamide. Upon charging of the first three reactants, the temperature rose from 27° to 31°C. and the solution became dark brown. The water content therein was less than 0.5 wt. %. Then dried carbon dioxide in excess was bubbled into the mixture and the temperature rose to 43°C. in 4 minutes and gradually returned to 32°C. at the end of the first hour. The temperature held at 31°C. for the next 2 hours. Total carbonation time was 3 hours at a temperature in the range of 31°–43°C.

The product after acidification and work-up was 1.6 grams of phenylpropiolic acid representing a yield of 37 mole % having a melting point of 137°–138°C. (lit. m.p. 137°–139°C.), a carbon content of 73.9 wt. % (74% calc.), a hydrogen content of 4.2 wt. % (4.1% calc.) and an infrared spectrum indentical to phenylpropiolic acid.

EXAMPLE III

This example illustrates the preparation of α-phenylcyanoacetic acid from benzyl cyanide.

The procedure of Example I was essentially repeated with the following exceptions:

To the reaction flask there was charged 3.5 grams of benzyl cyanide, 15.8 grams potassium phenoxide, and 75 mls. of dimethylformamide. The resultant mixture had a water content less than 0.5 wt. %. Within 3 minutes of charging the reactants to the flask the temperature rose from 31° to 45°C. and dropped to 32°C. over the next 19 minutes. Thereafter, the temperature during carbon dioxide bubbling remained between 28° and 32°C. for the reaction period. The total carbonation time was 4 hours. The temperature ranged in this 4 hour period between 28° and 45°C.

After acidification and work-up a solid was recovered in an amount of 2.7 grams and was determined to be α-phenylcyanoacetic acid in a yield of 56 mole %. The α-phenylcyanoacetic acid had a melting point of 92.5°–93.5°C. (lit. m.p. 92°C.) and infrared and nuclear magnetic resonance spectra which confirmed it to be α-phenylcyanoacetic acid. Elemental analysis found 67 wt. % C (calc. 67), 4.3 wt. % H (cal. 4.3) and 8.8 wt. % N (calc. 8.7).

EXAMPLE IV

This example illustrates the conversion of cyclopentadiene to tricyclo [5.2.1.0$^{2,6}$] deca-3,8-diene-4,9-dicarboxylic acid better known as Thiele's acid and a minor amount of tricyclo [5.2.1.0$^{2,6}$] deca-3,8-diene-5,5-dicarboxylic acid.

The procedure employed was that of Example I with the following exceptions:

There were introduced into the reaction flask 31.6 grams potassium phenoxide, 4.0 grams cyclopentadiene and 125 mls. of dimethylformamide. The resultant mixture had a water content of less than 0.5 wt. %. During carbon dioxide contact the temperature ranged from 33° to 47°C. over a period of 3 hours. The amount of carbon dioxide employed was in excess of that required for the complete conversion of the cyclopentadiene reactant to the carboxylic acid derivative.

One product recovered after work-up was determined to be Thiele's acid in an amount of 3.1 grams representing a 47 mole % yield and having a melting point of 199°–201°C. (lit. m.p. 197°–199°C.). Its nuclear magnetic resonance and infrared spectra confirmed it to be Thiele's acid. A minor amount of tricyclo [5.2.1.0$^{2,6}$] deca-3,8-diene-5,5-dicarboxylic acid was also found.

EXAMPLE V

This example further illustrates the method of the invention and is directed to a series of runs of the type found in Examples I-IV except sodium phenoxide is substituted for potassium phenoxide.

The test data and results are reported below in Table I:

TABLE I

| Run No. | $C_6H_5ONa$, g. | DMF, mls. | Reactant g. | Conditions of $CO_2$ Addition Temp., °C. | Time, Hrs. | Prod., mole % Yield |
|---|---|---|---|---|---|---|
| A | 27.8 | 100 | ID, 7.0 g | 32–60 | 5 | IC, 49 |
| B | 13.9 | 75 | BC, 3.5 g | 33–48 | 5 | PC, 60 |
| C | 13.9 | 75 | PA, 6.2 g | 30–43 | 4 | PP, 58 |
| D | 27.8 | 125 | CP, 4.0 g | 33–53 | 4 | T, 43 |

| | | |
|---|---|---|
| DMF | = | Dimethylformamide |
| ID | = | Indene |
| BC | = | Benzyl Cyanide |
| PA | = | Phenylacetylene |
| CP | = | Cyclopentadiene |
| IC | = | Indene-3-carboxylic acid |
| PC | = | α-Phenylcyanoacetic acid |
| PP | = | Phenylpropiolic acid |
| T | = | Thiele's Acid |

EXAMPLE VI

This example illustrates the criticality of the particular combination of base and organic reactant in the production of carboxylic acids.

The procedure employed is essentially that described in Example I. The test data and results are reported below in Table II:

TABLE II

| Run No. | Base, mole | DMF mls. | Org. React. | Reaction Conditions During $CO_2$ Addition Temp.,°C. | Time, Hrs. | COOH Prod. |
|---|---|---|---|---|---|---|
| AA | $C_6H_5OK$ 0.1 | 75 | p-NT | 23–44 | 2.2 | None |
| BB | '' 0.19 | 100 | CH | 28–38 | 4 | None |
| CC | '' 0.12 | 75 | FL | 23–27 | 5 | None |
| DD | IR-400 0.04 | 75 | PA | 27–30 | 2 | None |
| EE | NaOH 0.24 | 75 | p-NT | 32–40 | 4.8 | None |
| FF | $C_6H_5ONa$ 0.12 | 100 | ID | 31–60 | 2 | None |
| GG | IR-400 0.06 | — | ID | 46–51 ($CO_2$-1000 psig) | 8 | None |

| | | |
|---|---|---|
| IR-400 | = | Polystyrene quaternary amine |
| p-NT | = | p-Nitrotoluene |
| CH | = | Cyclohexanone |
| FL | = | Fluorene |
| PA | = | Phenylacetylene |
| ID | = | Indene |

As can be seen from the above table, substitution of organo and base reactants of a closely related nature for those contemplated herein fail to produce a carboxylic acid derivative.

We claim:

1. A method of producing tricyclo-[5.2.1.0$^{2,6}$] deca-3,8-diene-4,9-dicarboxylic acid and tricyclo-[5.2.1.0$^{2,6}$] deca-3,8-diene-5,5-dicarboxylic acid, comprising contacting cyclopentadiene with carbon dioxide under substantially anhydrous conditions in the presence of the base of the formula:

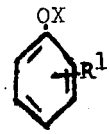

where X is sodium or potassium and R$^1$ is hydrogen or alkyl of 1 to 12 carbons, at a temperature between about 0° and 150°C. under a carbon dioxide pressure between about 1 and 200 atmospheres utilizing a mole ratio of base to organic compound of between about 1:1 and 20:1, subsequently acidifying the resultant reaction mixture to a pH of less than about 6 and recovering the carboxylic acid compound from the acidified mixture.

2. A method in accordance with claim 1 wherein said acidifying is conducted to a pH of between about 1 and 3.

3. A method in accordance with claim 2 wherein said acidifying is conducted with hydrochloric acid.

4. A method in accordance with claim 3 wherein said $CO_2$ contacting is conducted in the presence of between about 50 and 90 wt. % dimethylformamide.